(12) United States Patent
Flock et al.

(10) Patent No.: US 8,226,363 B2
(45) Date of Patent: *Jul. 24, 2012

(54) TURBINE WHEEL FOR A GAS OPERATED MEDICAL HANDPIECE AND MEDICAL HANDPIECE HAVING A TURBINE WHEEL, AND METHOD FOR MILLING A BLADE OF A TURBINE WHEEL

(75) Inventors: Alexander Flock, Biberach (DE); Helmut Gruber, Buxheim (DE); Thomas Roesch, Warthausen (DE)

(73) Assignee: Kaltenbach & Voigt GmbH, Biberach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/729,736

(22) Filed: Mar. 23, 2010

(65) Prior Publication Data

US 2010/0203472 A1 Aug. 12, 2010

Related U.S. Application Data

(63) Continuation of application No. 11/399,239, filed on Apr. 6, 2006, now Pat. No. 7,811,056.

(30) Foreign Application Priority Data

Apr. 7, 2005 (DE) .......................... 10 2005 016 035

(51) Int. Cl.
*A61C 1/05* (2006.01)
*F04D 29/26* (2006.01)

(52) U.S. Cl. ..... 415/202; 415/904; 416/185; 416/197 R; 416/237; 416/238; 416/243; 416/DIG. 2; 433/132

(58) Field of Classification Search ................. 415/202, 415/904; 416/197 R, 197 A, 197 B, 237, 416/238, 243, DIG. 2, 183, 185, 186 R; 433/132
See application file for complete search history.

(56) References Cited

U.S. PATENT DOCUMENTS 4,326,846 A * 4/1982 Sugai et al. ................... 433/132
4,505,677 A 3/1985 Nakayama et al.
(Continued)

FOREIGN PATENT DOCUMENTS

DE 33 22 146 A1 12/1983
(Continued)

OTHER PUBLICATIONS

European Search Report for Application No. DE 02005016035, dated Nov. 8, 2005.

*Primary Examiner* — Christopher Verdier
(74) *Attorney, Agent, or Firm* — Marshall, Gerstein & Borun LLP

(57) ABSTRACT

A turbine wheel for a gas operated medical handpiece includes a plurality of blades which extend in radial direction from a hub and extend in axial direction from a side ring web of the turbine wheel, and the front side of which is substantially concavely curved about an approximately radially running first axis of curvature. In order to increase the drive power or to better exploit the drive power at least one blade has at least in an axial end region an inclination surface which is inclined in the axial direction towards the front side.

10 Claims, 3 Drawing Sheets

U.S. PATENT DOCUMENTS

| | | |
|---|---|---|
| 5,364,227 A | 11/1994 | Franetzki et al. |
| 5,902,108 A | 5/1999 | Nakayama et al. |
| 6,120,291 A | 9/2000 | Bareth et al. |
| 6,676,374 B2 | 1/2004 | Hashimoto et al. |
| 7,811,056 B2 * | 10/2010 | Flock et al. .................. 415/202 |
| 2003/0190583 A1 | 10/2003 | Kuhn |

FOREIGN PATENT DOCUMENTS

| | | |
|---|---|---|
| DE | 198 07 566 A1 | 9/1998 |
| DE | 198 33 249 A1 | 1/2000 |

* cited by examiner

TURBINE WHEEL FOR A GAS OPERATED MEDICAL HANDPIECE AND MEDICAL HANDPIECE HAVING A TURBINE WHEEL, AND METHOD FOR MILLING A BLADE OF A TURBINE WHEEL

RELATED APPLICATIONS

This is a continuation of U.S. patent application Ser. No. 11/399,239, filed Apr. 6, 2006, now U.S. Pat. No. 7,811,056 the disclosure of which is hereby incorporated by reference herein.

BACKGROUND OF THE INVENTION

1. Field of the Invention

The invention relates to a turbine wheel for a gas operated medical, in particular dental-medical, handpiece and such a handpiece having a turbine wheel, and a method for milling blades of the turbine wheel.

2. Description of Related Technology

A turbine wheel and a handpiece of these kinds are described in DE 198 33 249 A1. In the case of this previously known turbine wheel or handpiece, the blades of the turbine wheel have at their front side, which can be acted upon with compressed air, in each case a concave circular arc section forming a curvature surface, the axis of curvature of which develops approximately radially, the handpiece having a delivery line for compressed air, the outlet of which is directed secantially at a side edge region of the blades. As a consequence, in operation of the turbine wheel or of the handpiece, the compressed air flow is in each case deflected at the curved front side, whereby it leaves the front side in the axially opposite edge region. Through this, the airflow not only gives up its impact energy to the respective blade, but also an additional energy, brought about by means of the deflection, which increases the power of the turbine drive.

In the case of a turbine wheel or handpiece of the kinds concerned here there is fundamentally required a high power exploitation and in particular power increase. This is because the turbine wheel or the handpiece should have, in particular in its forward region, a structural size which is as small as possible, so that upon treatment or working of the human or animal body, or an artificial part thereof, the view of the treatment site is affected as little as possible. This applies in particular for treatment sites in body cavities, in which the available space is restricted, such as is the case in the mouth of a patient or model head, with regard to a dental-medical handpiece. The greater is the delivered power of the turbine drive, the smaller can this, or the turbine wheel, or the region of the handpiece concerned, be formed, and a thus greater field of view of the operation site stands available to the operator.

SUMMARY

The object of the invention is thus, with a turbine wheel or a handpiece of the kinds indicated in the introduction, to increase the drive power or to better exploit the drive power.

In the case of the turbine wheel, and the handpiece in accordance with the invention, the rear side of the blades is, at least in one axial end region, inclined towards the front side. Through this the blades are given in each case a flow-favourable form, so that during the rotation of the turbine wheel they apply less resistance to the drive air flow, with the consequence that the drive power is better exploited and a greater delivered power is attained. Thereby it is to be taken into account that the front side of the blade acted upon by the pressure fluid is maintained in its surface size and thus from this aspect no adverse effect is present.

The inclination surface in accordance with the invention is, in its extension towards the end of the blade, curved towards the front side. This configuration is particularly flow favorable. Beyond this, the inclination surface may be inclined in the circumferential direction opposite to the direction of rotation of the turbine wheel, and thus likewise towards the front side. This additional inclination can be attained e.g. in that the axis of curvature, with regard to the rear side of the blade, is angularly offset by an acute angle, in the circumferential direction counter to the direction of rotation.

In another case of a turbine wheel or handpiece in accordance with the invention, the front side of the blades is formed hollow in radial direction. By means of this surface form of the front side the power is likewise better exploited or the delivered power is increased, because the pressure fluid flow at the hollow front side finds a greater resistance and thus the energy of the pressure fluid flow can be better exploited. Beyond this, the angle of the front side or front surface, in particular in the radially outer region of the blade, is also then favorable with reference to the incident pressure fluid, if the respective blade in rotational operation distances itself from the delivery pipe of the pressure fluid. Thus, due to this curvature in accordance with the invention, the power is better exploited or increased, because the hollow surface increasedly deflects the incident air flow and the thereby arising impact and deflection energy delivered to the blade.

In yet another case of a turbine wheel or handpiece in accordance with the invention, a longitudinal middle plane intersecting the apex of the blade, in the middle axial region of the apex, and the rear side of the blade, include an acute angle which is smaller than 38°. Through this, the rear surface of the blade is so formed that it on the one hand makes possible a more inclined incident angle of the pressure fluid flow and on the other hand a larger front side of the blade, through which the drive energy is likewise better exploited and the power improved. Beyond this, this configuration fulfills the purpose of generating on the suction side no surface for a counter-rotation moment.

The configurations in accordance with the invention are suitable in particular for such a turbine wheel with which at the side of the blades, towards which the pressure fluid exits, a ring groove is present into which the pressure fluid flows axially upon leaving the blades.

The configurations in accordance with the invention are, beyond this, particularly well suited for a turbine wheel or a handpiece having such a turbine wheel with which in the end region lying axially opposite the inclination surface, a ring web is arranged which closes the blade gaps on the side concerned. With such a configuration it is advantageous to direct the delivery pipe for the pressure fluid obliquely into the corner region between the ring web and the blades. Through this, the action of the pressure fluid on the front side of the blades is further improved.

The invention relates also to an advantageous method, with which a hollow-formed front side can be produced simply, rapidly and economically with an end milling cutter. Thereby this form milling can be carried out in the course of a combined movement of the end milling cutter in one pass, i.e. without of interruption of movement. Of particular advantage is that a form of the front side is self-actingly provided in simple manner which from a curvature form at the front side transitions in a rounded manner into a radially developing plane surface form.

BRIEF DESCRIPTION OF THE DRAWINGS

Below, the invention and further advantages that can be achieved thereby will be explained in more detail with reference to advantageous configurations of a preferred example. There is shown.

DETAILED DESCRIPTION

Figure 1:
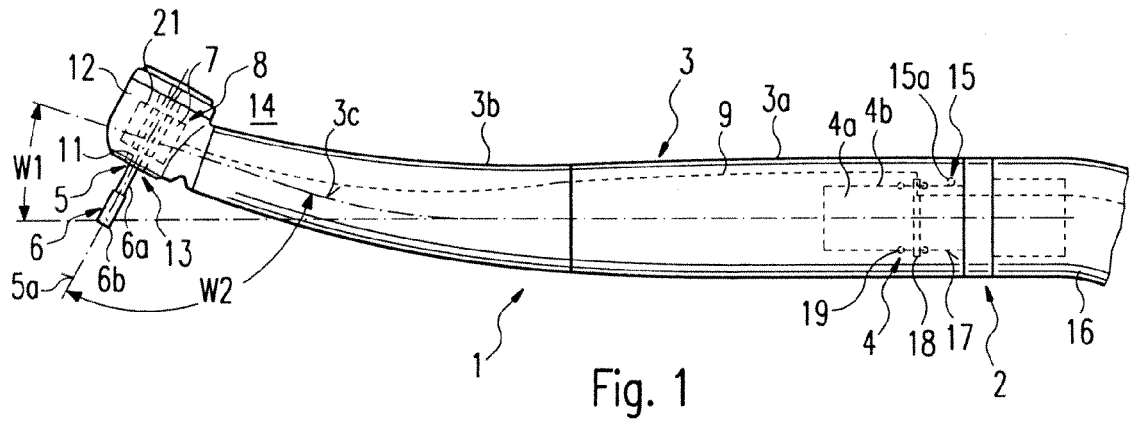
FIG. 1 is a side view of a dental-medical treatment instrument having a handpiece in accordance with the invention.

Referring to FIG. 1, main parts of the treatment instrument, generally designated by 1, are a connection part 2 forming a rearward end of the treatment instrument 1, a handpiece 3, which is releasably connected with the connection part 2 by means of a quick coupling 4 in the form of a plug-in coupling, in particular a plug-in/turn coupling, and which handpiece in the coupled condition extends forwardly in the form of an elongate or rod-like grip part 3a from the connection part 2, a holder device 5, for a treatment or working tool 6, arranged in a forward end region of the handpiece 3, and a turbine 8, which is integrated in the forward end region of the grip part 3a.

A compressed air line 9 extends to the turbine 8 longitudinally through the treatment instrument 1, and if applicable also a delivery line for consumed compressed air.

The holder device 5 is formed by means of a receiving sleeve 11 rotatably mounted in the grip part 3a and preferably extending transversely of the grip part 3a, on which receiving sleeve a turbine wheel 7 of the turbine 8 sits and which is rotatably mounted in the preferably thickened handpiece head 12 of the handpiece 3. The receiving sleeve 11 is open at its one end, through which there is formed an insertion opening 13 for a shaft 6a of the tool 6, the working section of which, abrasive or provided with cutting edges, is designated by 6b. The forward grip part section 3b having the handpiece head 12 may be straight with respect to the rearward grip part section 3a or may be arranged to be bowed or angled towards the side 14 of the handpiece 3 away from the insertion opening 13, whereby the acute angle W1 may be in the angle range between 10° and 28°, and may preferably be about 19°.

The angle W2 included between the longitudinal middle axis 3c and the middle axis 5a of the holding device 5 for the tool 6 may be a right angle or an obtuse angle, which is for example about 95° to 110°, in particular about 100° to 105°.

By means of the quick-coupling 4, the handiness of the handpiece 3 is significantly improved, because the connection part 2 does not need to take part in rotational movement of the handpiece 3 during the treatment or the working, and thus a rotational compensation can take place. The plug-in/turn coupling has a hollow cylindrical coupling pin 4a on one coupling part and a coupling recess 4b receiving the coupling pin 4a with slight play for movement. In the case of the present configuration, the coupling pin 4a extends forwardly from the connection part 2 and the coupling recess 4b is arranged in the rearward end region of the handpiece 3. For releasable positioning of the plug-in coupling in the coupling position there serves a latching device 15, which can be manually overcome, having a latch element 15a, mounted transversely movably, which is arranged in a recess in the outer envelope surface of the plug-in pin 4a or in the inner envelope surface of the plug-in recess 4b, and by means of an elastic spring force is so urged into a latch recess arranged in the respectively oppositely lying other part that the latch element 15a can spring out and the latch device 15 can be overcome by means of axially directed and manually easily applicable pulling force.

The connection part 2 is connected with a non-illustrated control apparatus, by means of a schematically illustrated flexible supply line 16, in particular by means of a flexible supply hose, connected with the connection part 2, as is per se known in the case of a medical or dental-medical treatment station. The delivery line 9 extends through the supply line 16 and through the treatment instrument 1 and there may extend also at least one further medium line, e.g. for light, air, water and/or spray, which extend so through the quick-coupling 4 that passage in the medium line or lines is ensured in any rotational position. The at least one delivery line 9 may pass through the dividing joint 17 between the plug-in pin 4a and the plug-in recess 4b in a Z-form in a ring groove 18, whereby the section of the delivery line radially passing through the dividing joint 17 is sealed off by means of sealing rings 19 arranged to the two sides of the ring groove 18, which sealing rings are arranged in an outer ring groove of the plug-in pin 4a or in an inner ring groove of the plug-in recess 4b.

The turbine 8 has a turbine wheel 7 which is rotatably mounted in a e.g. hollow cylindrical turbine chamber 21 and has at its periphery a plurality, e.g. 7 or 8, blades 22 (FIG. 2), which are formed in each case in the same rotary position the same as one another, so that in the following only one blade 22 needs to be described.

Figure 2:
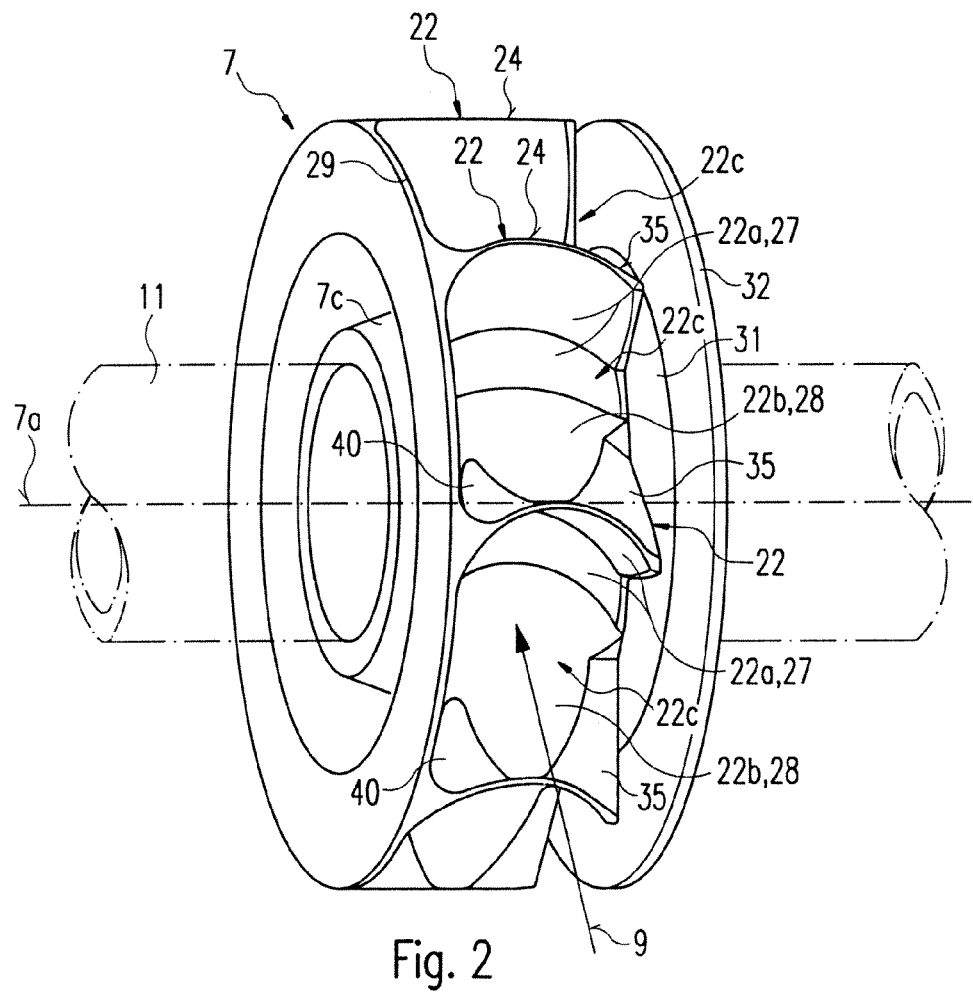
FIG. 2 is a perspective view of a turbine wheel of the treatment instrument of FIG. 1.
Figure 3:
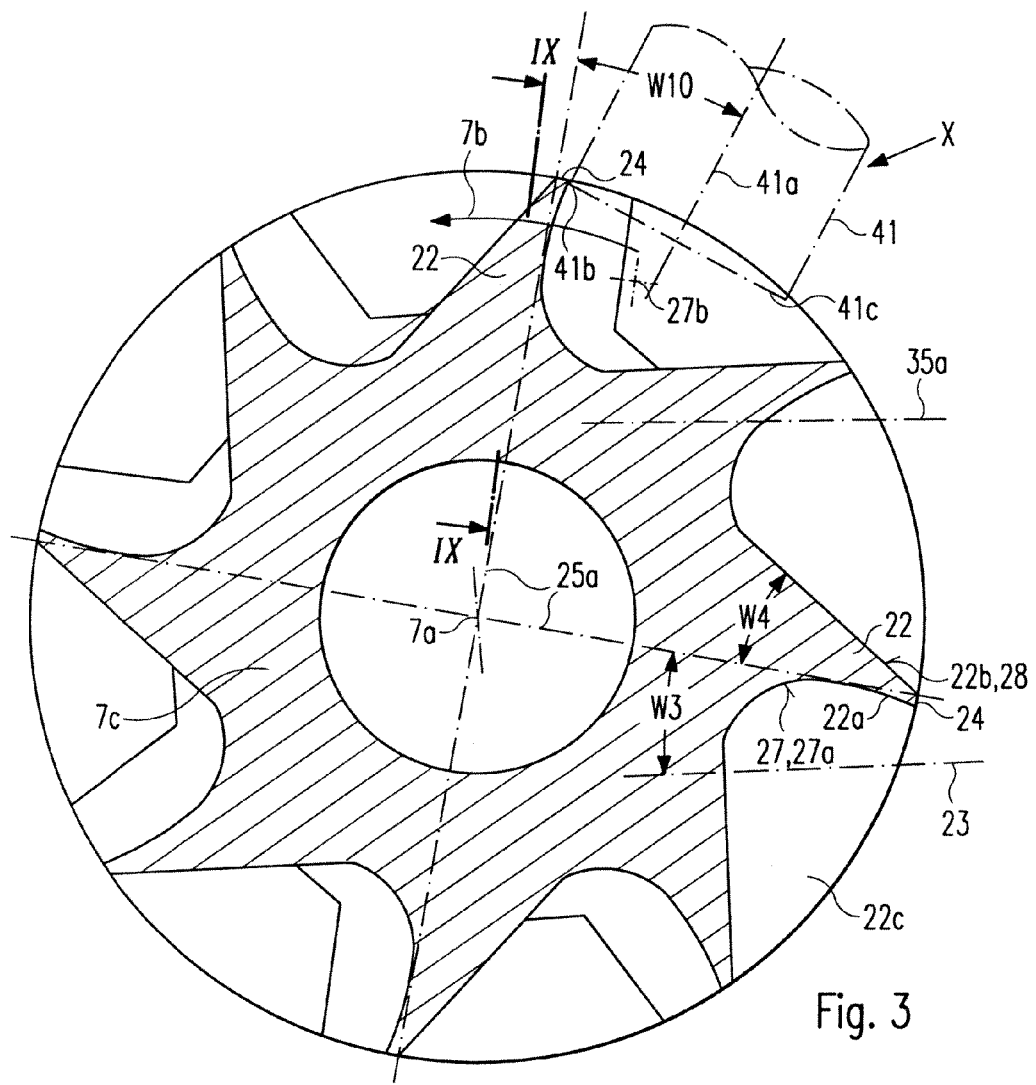
FIG. 3 is a radial middle cross-section of the turbine wheel of FIG. 2.
Figure 6:
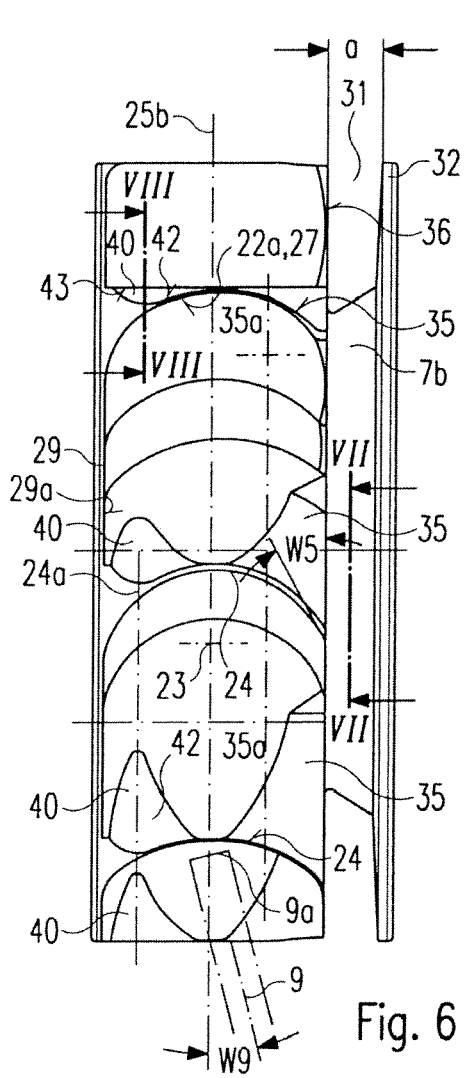
FIG. 6 is a radial view of the turbine wheel of FIG. 2.

As can best be understood from FIGS. 2 and 6, the delivery line 9 opens out—seen longitudinally of the axis of rotation 7a—secantially into the turbine chamber 21, whereby the side towards the inlet opening 9a of at least one axially extending blade 22 is designated as front side 22a and the side of the blade 22, preferably planar, away from the inlet opening 9a is designated as rear side 22b. The front side 22a is formed concavely in a secantial plane and in a radial plane, and thus spherically formed. The front side 22a is, with regard to a first axis of curvature 23, illustrated in FIGS. 3 and 6, preferably curved uniformly and thus circular arc section shaped, whereby the axis of curvature 23 extends at right angles to the rear side 22b of the neighboring blade 22 and includes with a longitudinal middle plane 25a, intersecting the apex of the other neighboring blade 22 and the axis of rotation 7a, an acute angle W3. This angle W3, which is about 9° to 19°, in particular about 13°, is open towards the axis of rotation 7a.

Further, the front side 22a or the blade surface 27 is concavely curved in the radial cross-sectional plane, whereby this line of curvature 27a is preferably radially inwardly progressively curved, i.e. more strongly curved with increasing distance from the periphery. Both curvatures provide a spherically curved blade surface 27, which extends over the entire front side 22a. For better orientation there is indicated, see FIG. 3, and designated by 27b, an axis of curvature of the line of curvature 27a developing in the middle radial section, substantially emphasizing a curvature middle point.

The rear side 22b of the blade 22 has a plane exit surface 28 which includes with the longitudinal middle plane 25a an acute angle W4 of about 26° to 36°, in particular about 32°, which is open towards the periphery.

The blade 22 extends on a side of the turbine wheel 7, in the case of the exemplary embodiment on the side towards the insertion opening 13, from a thin radial ring web 29, which connects and stabilizes the axial ends of the blades 22 theretowards and at the same time bounds with a substantially radial inner side surface 29a the blade space 22c present between the front side 22a of the one blade 22 and the rear side 22b of the blade 22 neighboring in the circumferential direction.

On the axially oppositely lying side, such a ring web 29 is not present, and thus the blade space 22c is open to the side, and it opens into a ring chamber 31 which thus is open with regard to all blade spaces 22c and at an axial spacing a from the blade 22 is bounded by means of a second ring web 32 which extends in substance radially outwardly from a turbine wheel hub 7c also carrying the blade 22 and ends at the radial height of the apexes 24 of the blades 22.

At the end of the blades 22 lying axially opposite to the ring web 29, or at the run-out into the ring chamber 31, the blade surfaces 27, in each case curved around the approximately radial axis of curvature 23, intersect the side surfaces 36 of the blades 22 present at the run-out. Thereby, the front sides 22a, or tangents extending thereon, include with the side surfaces 36 an acute angle W5, which is smaller than about 35°, in particular being about 10° to 30°.

Figure 9:
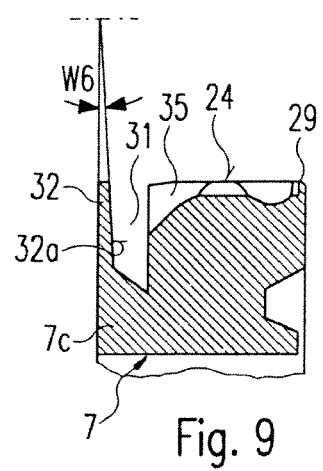
FIG. 9 is the partial section IX-IX of FIG. 3.

The inner side surface 32a of the second ring web 32 can be formed outwardly divergently and may include with the outer side radial plane of the ring web 32, or of the turbine wheel 7, an acute angle W6 of about 3° (FIG. 9). The base surface of the ring chamber 31 is formed divergently towards the ring web 32. A conical surface may include an acute angle with the axis of rotation 7a.

The rear side 22b of the blades 22 is in each case in one or in both axial end regions axially inclined, preferably curved, towards the front side 22a with an inclination surface 35. In the case of the exemplary embodiment, the curvature in the end region towards the ring chamber 31 is formed by means of a convex curvature surface, which preferably extends over the in substance entire radial height h of the corner region between the rear side 22b and the associated side surface 36 of the blades 22, here the side surface towards the ring chamber 31, is inclined towards the front side 22a of the blade 22 and thereby roundedly breaks the corner present with the known configuration. Within the scope of the invention the axially inclined development of the rear side 22b thereby formed may also be formed by means of a oblique surface forming the inclination, which is not illustrated for reasons of simplification.

The axially inclined and thereby plane or curved surface 35 is preferably also inclined in radial direction or circumferential direction, and with increasing spacing from the axis of rotation 7a progressively in the sense of a radial inclination. Through this, the free space provided by means of the axial inclination is also increased axially outwardly and the air flow flowing through the blade space 22c in rotary operation of the turbine wheel 7 can in the above-described corner regions also be better carried off by means of this radial inclination, through which the corner region offers less resistance to the air flow, which leads to an improved use of power and to an increase of the delivered power.

Figure 7:
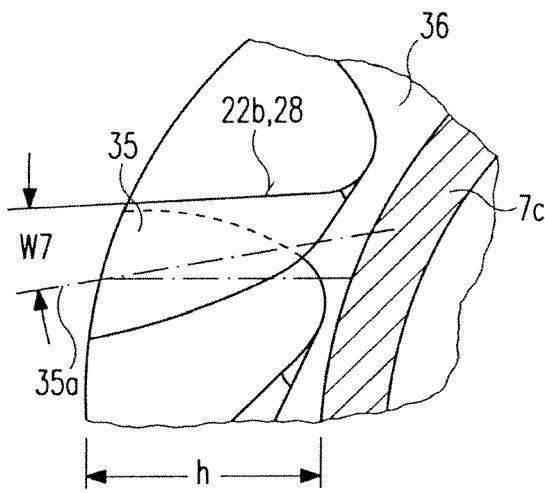
FIG. 7 is the partial section VII-VII of FIG. 6.

The radially outwardly directed inclination can be achieved in that the axis of curvature 35a of the curvature surface 35, preferably running parallel to the transverse middle plane 25b, is inclined against the direction of rotation 7b with respect to the rear side 22b. In FIG. 7 this inclination angle of the axis of curvature 35a, which is about 5° to 15°, in particular about 10°, is designated by W7.

In the other axial end region of the rear side 22b, in the exemplary embodiment, the axially directed inclination towards the front side 22a is formed by means of a groove 40, which with its flank towards the rear side middle forms the inclined surface. In the exemplary embodiment this flank is likewise formed by means of a curvature surface 42, see FIG. 6.

Otherwise, the base of the groove 40 is concavely rounded and the flank 43 of the groove 40 lying opposite the curvature surface 42 can run out at the inner side surface 29a or at a small spacing therefrom, at the rear side 22b, as is realized in the case of the exemplary embodiment.

Figure 8:
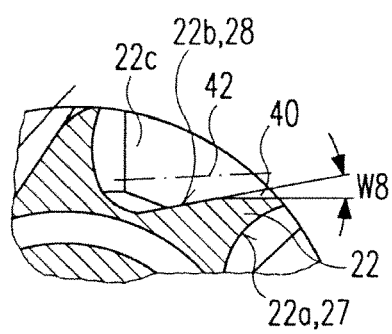
FIG. 8 is the partial section VIII-VIII of FIG. 6.

The width of the curvature surface 42 is preferably progressive with increasing distance from the axis of rotation 7a. In the case of the exemplary embodiment this is achieved in that the axis of curvature 42a of the curvature surface 42 and/or groove 40 or the base surface of the groove 40 is, with reference to the rear side 22b, inclined against the direction of rotation 7b of the turbine wheel 7a by the angle W8, which is about 5° to 15°, in particular about 10°, which is best understood from FIG. 8.

The radial inclination of the rear side 22b, directed towards the front side 22a, in the left axial end region, has particular advantages because in the case of the exemplary embodiment in the left axial end region the air flow does not open out to the side. In this axial end region, through this radial inclination, the advantage is achieved that the blade space 22a receives a greater free space in the circumferential direction, which at the apex 24 leads to the apex extension present in the axial end region between the blade spaces 22c neighboring one another and formed by means of a gusset shaped envelope surface section 24a, being reduced. This is of advantage because the envelope surface section 24a affects the effectiveness of the air flow emerging out of the inlet opening 9a. Through the reduction of the size of the envelope surface section 24a this effect is reduced. Beyond this, this radial inclination leads to the respective blade space 22c acted upon with compressed air, with the continuing rotation, being able to be acted upon for a longer time and thus increasedly with the pressure medium. Both above described particular features thus lead to a further improvement of the use of power.

Beyond this, through the two above-described inclination surfaces 35, 42 there is less material present in the axial end regions and thus the weight of the turbine wheel 7 is reduced, which likewise contributes to its power increase and accelerates the starting of the turbine wheel 7, and reduces running on.

As can be understood in particular from FIGS. 2 and 6, the delivery line 9 is, with reference to a transverse middle plane 25, inclined towards the axial direction away from the ring chamber 31, whereby this angle of inclination W9 may be about 5° to 15°, in particular about 10°. Thereby, the inlet opening 9a may be arranged in the middle region of the blades 22 or in the half of the blades which neighbors the ring chamber 31.

Below there will be described a particular circumstance which relates to the spherical form of the front side 22a or blade surface 27 of the blades 22. This particular form consists in that the front side 22a or blade surface 27 runs out so curved into the inner side surface 29a that this forms a tangent with reference to the curvature of the blade surface 27. Through this there is achieved a uniform and disruption free directing of air flow, which likewise contributes to an improved power exploitation.

Below, method features of an advantageous method for the production of the two curvature surfaces, curved around two axes of curvature 23, 27b running transversely of one another, of the front side 22a or blade surface 27 will be described.

It is known to mill the rear side 22b and a front side 22a, curved only about the first axis of curvature 23, at the same time by means of a cylindrical end milling cutter, the end face of which is plane. Such an end milling cutter is so secantially moved into the envelop surface of the turbine wheel 7, in an angular position in which its middle axis runs at right angles to the rear side 22b, that the end milling cutter first mills the rear side 22b and at the end of its advancing movement mills the front side 22a, wherein the curvature thereof is determined by the circumferential curvature of the end milling cutter.

Figure 4:
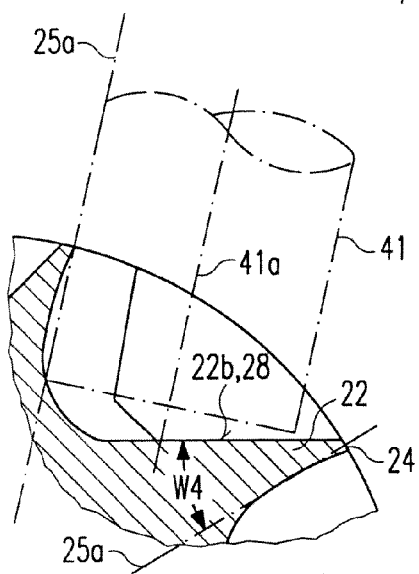
FIG. 4 is the detail designated in FIG. 3 by X showing a first working position of a milling cutter.

In the case of the method in accordance with the invention, in contrast, both curvatures of the spherical curvature of the blade surface 27 are simultaneously milled, wherein e.g. likewise a cylindrical end milling cutter 41 can be employed. With this method, the end milling cutter 41, from a starting position illustrated at the top in FIG. 3, arranged centrally with reference to the transverse middle plane 25b, in which the longitudinal middle axis 41a of the end milling cutter includes a radially outwardly open acute angle W10 (FIG. 3) with a longitudinal middle plane 25a intersecting the axis of rotation 7a and the associated blade apex 24, and its forward edge 41b touches the apex of the blade 22, is rearwardly inwardly sunken with reference to the turbine wheel 7 and at the same time pivoted with a pivot movement reducing the acute angle W10. This milling movement, combined of the sinking movement and the pivoting movement, is continued until the preferably planar end face 41c of the end milling 41 corresponds to the desired position of the rear side 22b or rear surface 28 of the blade 22, which is shown by the draftsman's illustration in FIG. 5. With this milling movement, the cutter 41 mills the blade surface 27 with the rounded curvature line 27a, which may be uniformly curved or radially inwardly progressively curved and can run out in this with tangential arrangement of the exit surface 28, or can run out in this with an obtuse angle. Through this there is created a concave blade surface 27 which transitions in a stepless manner into the inner surface 29a of the ring web 29, which preferably develops in a radial transverse plane. The pivot position of the cutter 41 shown in FIG. 4 shows a middle position in the case of the above-described milling movement.

Figure 5:
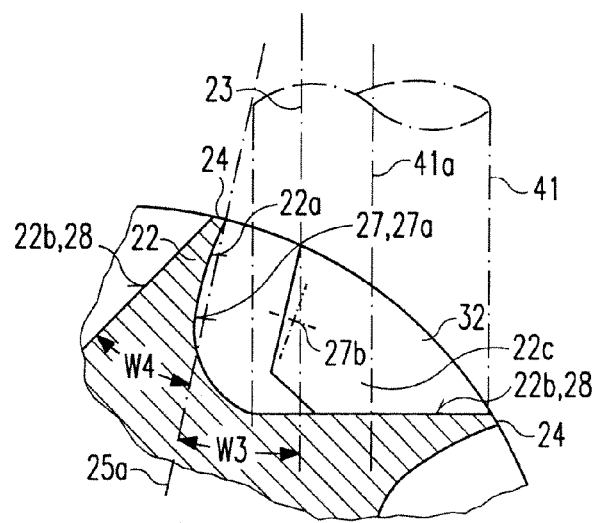
FIG. 5 is the detail designated in FIG. 3 by X showing a second working position of the milling cutter.

As the next method step, which can follow on from the above-described milling movement without coming to rest, the cutter 41 is moved into the position in accordance with FIG. 5 along the exit surface 27 and outwardly moved in the radial transverse plane 25b, whereby it finishes the outer regions of the rear surface 28 and of the inner surface 29a.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A turbine wheel for a gas operated medical handpiece, comprising:
   a plurality of blades which extend in radial direction from a hub and extend in an axial end region up to a ring recess in the turbine wheel, at least one blade having a front side which is substantially formed concavely in a secantial plane and in a radial plane, the front side having a partially spherical surface, and
   a rear side having, at least in an axial end region, an inclination surface which is inclined in the axial direction towards the front side.

2. The turbine wheel according to claim 1, wherein the inclination surface is convexly curved towards the front side.

3. The turbine wheel according to claim 2, wherein the inclination surface is also inclined in the circumferential direction opposite to the direction of rotation of the turbine wheel.

4. The turbine wheel according to claim 3, wherein seen along the axis of rotation, the inclination surface is inclined, with reference to a non-inclined section of the rear side, by an angle of between about 5° and about 15°.

5. The turbine wheel according to claim 1, wherein the rear side of the blades is provided in the other axial end region with an inflow groove, which has a rounded cross-sectional form.

6. A turbine wheel according to claim 1, wherein the front surface includes a first axis of curvature and a second axis of curvature.

7. A turbine wheel according to claim 6, wherein the first axis of curvature extends perpendicularly to a rear side of a neighboring blade.

8. A medical handpiece, comprising:
   an elongate grip part;
   a holder device for a tool rotatably mounted in a forward end region of the elongate grip part;
   a turbine wheel rotatably mounted in the handpiece and drivably connected to the holder device; and
   a delivery line for a gas that directs emerging gas flow against the turbine wheel;
   wherein the turbine wheel has a plurality of blades extending from a hub and a ring web connecting the plurality of blades along one side of the plurality of blades, another side of the plurality of blades remaining unattached to the ring web forming free blade ends, a front side of each blade being concavely curved about an approximately radially running first axis of curvature, a rear side of each blade being convexly curved toward the front side, the delivery line being directed against the front side of each blade and angled away from the free blade ends and the front side of each blade being hollow in radial direction.

9. A turbine wheel according to claim 6, wherein the first axis of curvature is transverse to the second axis of curvature.

10. A handpiece according to claim 8, wherein the emerging gas flow is directed away from the free blade ends at an angle of between 5° and 15° with respect to a plane of the ring web.

* * * * *